United States Patent [19]

Achtermann et al.

[11] Patent Number: 4,702,604
[45] Date of Patent: Oct. 27, 1987

[54] PRECISE DETERMINATION OF THE COMPRESSIBILITY FACTOR OF A GAS FROM REFRACTIVE INDEX MEASUREMENTS

[75] Inventors: Jurgen H. Achtermann, Hanover, Fed. Rep. of Germany; Tapan K. Bose; Jean-Marie St-Arnaud, both of Trois-Rivières, Canada

[73] Assignee: L'Universite du Quebec a Trois-Rivieres, Quebec, Canada

[21] Appl. No.: 837,290

[22] Filed: Mar. 7, 1986

[30] Foreign Application Priority Data

Dec. 31, 1985 [CA] Canada .................................. 498839

[51] Int. Cl.$^4$ ........................ G01N 21/41; G01N 1/10
[52] U.S. Cl. .................................... 356/361; 356/128; 356/246
[58] Field of Search .............. 356/346, 354, 361, 128, 356/328, 246, 410

[56] References Cited

U.S. PATENT DOCUMENTS 4,229,105 10/1980 Silverbage ........................ 356/246

OTHER PUBLICATIONS

"An Apparatus for the Simultaneous Measurement of Equilibrium Phase Composition and Refractive Index Data at Low Temp. and High Pressures", Robinson, Cryogenics, 7–1975.

"Interferometric Techigues for Fundamental Static or Dynamic Pressure Measurements and Transducer Calibration", Jones et al., Journal of Physics E, 12–1977.

Primary Examiner—Davis L. Willis
Assistant Examiner—S. A. Turner
Attorney, Agent, or Firm—Charles E. Brown; Charles A. Brown

[57] ABSTRACT

A method and an apparatus for the precise determination of the compressibility factor of a gas sample are disclosed. Two grating interferometers are coupled together with one interferometer defining a refractive index interferometer adapted to provide a signal of information related to the refractive index of the gas sample and the other interferometer defining a pressure interferometer adapted to provide another signal of information related to the pressure of the gas sample whereby to permit measurement of the refractive index as a function of pressure. Each interferometer is capable of dividing a linearly polarized monochromatic laser beam into a measuring beam and a reference beam and causing the measuring beam and reference beam to travel along respective optical paths extending in close parallel relationship over predetermined optical path lengths. The refractive index interferometer and pressure interferometer comprise respectively two optical cells in tandem alignment and a single optical cell with each cell having elongated measuring and reference compartments arranged in close parallel relationship along the parallel optical paths of the measuring beam and reference beam to receive same therethrough, the measuring compartments of both cells of the refractive index interferometer being interconnected to permit gas expansion therebetween with the measuring compartment of one of the cells being connected to the measuring compartment of the single cell of the pressure interferometer via a pressure equilibrium chamber to provide the interferometer coupling. The expansion technique enables one to obtain accurate values for higher order terms of the Lorentz-Lorenz equation. This technique combined with the absolute measurements of the refractive index as a function of pressure leads to values of the compressibility factor comparable to the best PVT values, in a much shorter time as compared to other methods.

20 Claims, 10 Drawing Figures

— Nitrogen (for pressure measurement)
---- Gas under examination
C–O  Coupling of the two cells
0    Zero setting of the reversible counter (first measurement point)
0,1,2...N  Measurement points
N    Reference point (vacuum)

FIG. 9

PRECISE DETERMINATION OF THE COMPRESSIBILITY FACTOR OF A GAS FROM REFRACTIVE INDEX MEASUREMENTS

BACKGROUND OF THE INVENTION

The present invention relates to a method and apparatus for the interferometric determination of the compressibility factor of a gas. More particularly, the invention is directed toward the precise determination of the compressibility factor from refractive index measurements.

The compressibility factor measures the deviation from the ideal gas law which describes the behavior of a perfect gas. A perfect gas assumes that there are no interactions between molecules. Although a perfect gas does not exist, most gases at low densities resemble closely the perfect gas. A perfect gas follows an ideal gas law given by $$PV = nRT \quad (1)$$

where P is the pressure, V is the volume, R is the universal gas constant, T is the absolute temperature and n is the number of moles. An ideal gas, however, is totally inadequate to describe the behavior of high-pressure gases. The ideal gas equation (1) can be modified to handle real gases by inserting the compressibility factor Z. Thus, the gas law can now be written as $$PV = ZnRT \quad (2)$$

The compressibility factor which must be determined from experiments is a function of temperature, pressure and gas composition. The precision in the measurement of the compressibility factor is important both from the point of view of fundamental as well as applied science. In molecular physics the compressibility factor is a direct measure of the importance of molecular interactions. In gas industry the compressibility factor is necessary to calculate the cost of natural gas. The cost of gas which depends on the heat content is calculated on the basis of heat per unit mass. The mass m of natural gas is derived from the compressibility factor by using the formula $$m = MPV/ZRT \quad (3)$$

where M is the molecular weight.

Until now, the most commonly used methods for the determination of the compressibility factor have been the Burnett expansion technique and constant or variable volume methods. In one commercial application of the Burnett method, for example, the gas under test is contained at a measured pressure $P_1$ above atmospheric pressure in one chamber of volume $V_1$ of a double chamber vessel which is in a constant temperature bath. The second chamber has a volume $V_2$ usually at atmospheric pressure $P_2$. The test gas is expanded to fill both chambers and the pressure $P_3$ of the gas in the resultant volume $V_1 + V_2$ is measured. The compressibility factor $Z_1$ is given by:

$$Z_1 = \frac{P_1}{P_3 \frac{K+1}{Z_3} - P_2 \frac{K}{Z_2}} \quad (4)$$

where K is the ratio $V_1/V_2$, $Z_2$ and $Z_3$ are experimental values determined by iteration and represent respectively the compressibility factors at $P_2$ and $P_3$. Thus, the volume ratio K as well as the values of $Z_2$ and $Z_3$ must be determined experimentally. Although such a method enables one to determine the compressibility factor with a precision of about 0.01%, it is in general very time consuming particularly when use is made of a dead weight gauge to measure the pressure, in which case it may take several days to obtain a certain number of experimental values. Thus, only a limited number of experimental values can be obtained per unit of time with the Burnett method. The same applies with respect to the constant or variable volume methods.

SUMMARY OF THE INVENTION

It is therefore an object of the present invention to overcome the above drawback and to provide a method and apparatus enabling the determination of the compressibility factor of a gas in a more rapid manner than the prior art while still obtaining a precision of about 0.01%.

In accordance with one aspect of the invention, there is provided a method for the precise determination of the compressibility factor of a gas sample, wherein use is made of two grating interferometers coupled together with one interferometer defining a refractive index interferometer adapted to provide a signal of information related to the refractive index of the gas sample and the other interferometer defining a pressure interferometer adapted to provide another signal of information related to the pressure of the gas sample whereby to permit measurement of the refractive index as a function of pressure. Each interferometer is capable of dividing a linearly polarized monochromatic laser beam into a measuring beam and a reference beam and causing the measuring beam and reference beam to travel along respective optical paths extending in close parallel relationship over predetermined optical path lengths. The refractive index interferometer and pressure interferometer comprise respectively two optical cells in tandem alignment and a single optical cell with each cell having elongated measuring and reference compartments arranged in close parallel relationship along the parallel optical paths of the measuring beam and reference beam to receive same therethrough, the measuring compartments of both cells of the refractive index interferometer being interconnected to permit gas expansion therebetween with the measuring compartment of one of the cells being connected to the measuring compartment of the single cell of the pressure interferometer via a pressure equilibrium chamber to provide the interferometer coupling. The method according to the invention comprises the steps of:

(a) maintaining all the optical cells at a constant predetermined temperature value;

(b) filling the measuring compartments of the one cell and the single cell respectively with the gas sample and a selected gas at a same pressure above atmospheric pressure and allowing the gas sample and selected gas to reach thermodynamic equilibrium in the pressure equilibrium chamber;

(c) stepwise lowering the pressure of the gas sample and selected gas until substantially vacuum is attained in the measuring compartments of both the one cell and the single cell while maintaining the reference compartments thereof substantially under vacuum and recording at each step the signals of information provided by both interferometers once the thermodynamic equilibrium has been re-established in the pressure equilibrium chamber, thereby obtaining first and second sets of data;

(d) uncoupling the refractive index interferometer and pressure interferometer from one another;

(e) evacuating the measuring compartment of the other cell of the refractive index interferometer, re-filling the measuring compartment of the one cell with the gas sample at superatmospheric pressure, allowing the gas sample to reach thermodynamic equilibrium, recording the signal of information provided by the refractive index interferometer, causing the gas sample to expand into the measuring compartment of the other cell while maintaining the reference compartments of both the one cell and the other cell substantially under vacuum, and recording again the signal of information provided by the refractive index interferometer once the thermodynamic equilibrium of the gas sample has been re-established;

(f) evacuating the measuring compartments of both the one cell and the other cell, filling the measuring compartment of the other cell with the gas sample at a pressure equal to the superatmospheric pressure of step (e), allowing the gas sample to reach thermodynamic equilibrium, recording the signal of information provided by the refractive index interferometer, causing the gas sample to expand into the measuring compartment of the one cell while still maintaining the reference compartments of both the one cell and the other cell substantially under vacuum, and recording again the signal of information provided by the refractive index interferometer once the thermodynamic equilibrium of the gas sample has been re-established;

(g) repeating steps (e) and (f) several times as paired steps after evacuation of the measuring compartment of the one cell, each of the paired steps being carried out at a different pressure above atmospheric pressure, thereby obtaining a third set of data; and (h) processing the first, second and third sets of data obtained in steps (c) and (g) together with the temperature value of step (a) through circuitry means to obtain the compressibility factor of the gas sample.

The gas which is used in the pressure interferometer is selected for its well known or established thermodynamic properties. The selected gas is preferably an inert gas whose second pressure virial coefficient is low, for example nitrogen or argon.

The constant temperature at which all the optical cells are maintained is generally in the range of about 0° to about 100° C. To this end, the cells can be immersed in a thermostatic bath which allows passage of the measuring beam and reference beam without contacting the thermostatic liquid contained in the bath.

The pressure of the gas sample and selected gas in step (b) is in general selected from the range of about 100 to about 500 bars depending on the nature of the gas sample. The pressure of the gas sample in steps (e) and (f) is preferably selected from the range of about 50 to about 500 bars depending again on the nature of the gas sample, and steps (e) and (f) can be repeated at pressures either above or below the selected pressure.

According to a particularly preferred embodiment of the invention, the laser beam of each interferometer is a He-Ne laser beam polarized at 45° and the reference beam issued from such a laser beam is passed through a half-wavelength plate such that the measuring beam and reference beam have respective polarization planes which are perpendicular to one another. The measuring beam and reference beam of each interferometer after having travelled the predetermined optical path lengths are then focussed on a grating to produce three beams corresponding to selected superimposed diffraction orders including a zero order of diffraction, the three beams are rendered parallel and caused to impinge on a double refracting quartz plate with a quarter-wavelength plate being incorporated in the optical path of the beam of the zero order of diffraction to produce three pairs of phase modulated optical signals, each pair of optical signals being in-phase and anti-phase with one pair being in quadrature with the other two pairs, and the optical signals are converted into corresponding push-pull modulated electrical signals which are processed electronically to produce a d.c. compensated rotating electrical field associated with each interferometer. Thus, the thermodynamic equilibrium of the gas sample in steps (b), (c), (e) and (f) and of the selected gas in steps (b) and (c) can be conveniently ascertained by observing the stability of the electrical fields associated respectively with the refractive index interferometer and the pressure interferometer. Such a thermodynamic equilibrium is necessary in order to avoid the Joule-Thompson effect.

The present invention also provides, in a further aspect thereof, an apparatus for carrying out a method as defined above. The apparatus according to the invention comprises two grating interferometers coupled together with one interferometer defining a refractive index interferometer adapted to provide a signal of information related to the refractive index of the gas sample and the other interferometer defining a pressure interferometer adapted to provide another signal of information related to the pressure of the gas sample whereby to permit measurement of the refractive index as a function of pressure, each interferometer including means for dividing a linearly polarized monochromatic laser beam into a measuring beam and a reference beam and means for causing the measuring beam and reference beam to travel along respective optical paths extending in close parallel relationship over predetermined optical path lengths. The refractive index interferometer and pressure interferometer comprise respectively two optical cells in tandem alignment and a single optical cell with each cell having elongated measuring and reference compartments arranged in close parallel relationship along the parallel optical paths of the measuring beam and reference beam to receive same therethrough.

The apparatus of the invention further includes means for maintaining all the optical cells at a constant predetermined temperature value, first valved conduit means connecting the measuring compartment of one of the cells of the refractive index interferometer with the measuring compartment of the single cell of the pressure interferometer via a pressure equilibrium chamber to selectively couple or uncouple the interferometers, second valved conduit means interconnecting both cells of the refractive index interferometer to permit gas expansion therebetween when the interferometers are uncoupled and thereby enable the refractive index interferometer to provide a further signal of information, third valved conduit means adapted to connect a vacuum means to the reference compartments of all the cells for maintaining same substantially under vacuum and to the measuring compartments of both cells of the refractive index interferometer for evacuating same after the gas expansion, fourth valved conduit means adapted to connect a source of the gas sample to the measuring compartments of both cells of the refractive index interferometer for filling the measuring compartment of either cell with the gas sample at superatmospheric pressure, and fifth valved conduit means adapted to connect a source of a selected gas to the measuring compartment of the single cell of the pressure interferometer for filling same with the selected gas at superatmospheric pressure. The first and third valved conduit means are operative to stepwise lowering the pressure of the gas sample and selected gas until substantially vacuum is attained in the measuring compartments of both the one cell and the single cell when the interferometers are coupled. Circuitry means are also provided for processing the signals of information provided by both interferometers as a result of the pressure lowering and the gas expansion together with the temperature value to obtain the compressibility factor of the gas sample.

In order to prepare the output signal of each interferometer so as to be readily processed by the circuitry means, each interferometer preferably includes a He-Ne laser source means adapted to generate a monochromatic laser beam linearly polarized at 45° and a half-wavelength plate arranged in the optical paths of the reference beam issued from such a laser beam so that the measuring beam and reference beam have respective polarization planes which are perpendicular to one another. Each interferometer further includes means for focussing the measuring beam and reference beam after having travelled the predetermined optical path lengths on a grating to produce three beams corresponding to selected superposed diffraction orders including a zero order of diffraction; means for rendering the three beams parallel with one another; a double refracting quartz plate arranged in the optical paths of the three parallel beams with a quarter-wavelength plate being incorporated in the optical path of the beam of the zero order of diffraction to produce three pairs of phase-modulated optical signals, each pair of optical signals being in-phase and anti-phase with one pair being in quadrature with the other two pairs; and means for converting these optical signals into corresponding push-pull modulated electrical signals. The signal converting means of each interferometer has first, second and third outputs associated respectively with the three pairs of push-pull modulated electrical signals, the second output being associated with the pair of signals which is in quadrature with the other two pairs.

The circuitry means, on the other hand, preferably comprise first and second differential amplifiers associated with the signal converting means of each interferometer, the first differential amplifier having two inputs and an output and the second differential amplifier having an input and an output, the inputs of the first differential amplifier being connected to the first and third outputs of the signal converting means whereby to produce a d.c. compensated output signal and the input of the second differential amplifier being connected to the second output of the signal converting means. A phase detector having two inputs and an output has its inputs connected to the outputs of the first and second differential amplifiers whereby to produce a d.c. compensated rotating electrical field at the output of the phase detector. A counter having an input and an output has its input connected to the output of the phase detector whereby to produce at the output of the counter a fringe count associated with each interferometer. A micro-processor is connected to the counter of each interferometer for processing the fringe count associated therewith together with the aforesaid predetermined temperature value to obtain the compressibility factor of the gas sample.

In a preferred embodiment, the measuring compartments of both cells of the refractive index interferometer have substantially equal volumes and lengths in order to facilitate the measurements and the interpretation of the results. On the other hand, the measuring compartment of the single cell of the pressure interferometer preferably has a volume substantially twice the volume of either cell of the refractive index interferometer, for increased accuracy.

In another preferred embodiment of the invention, the measuring compartment of each cell is provided with gas inlet and outlet means in gas flow communication with gas permeable lining means extending longitudinally of the measuring compartment over the whole length thereof, the gas permeable lining means allowing uniform gas distribution or evacuation over substantially the whole compartment length. This avoids local turbulence which would otherwise be caused by gas entering the measuring compartment at a single point, and thus ensures stability of the measuring beam passing through the measuring compartment. The internal volume of the measuring compartment is also reduced by the provision of such gas permeable lining means so that on one hand a lesser quantity of gas sample is necessitated which may be important in the case of expensive gases and, on the other hand, the thermodynamic equilibrium is reached more rapidly. Preferably, both the measuring compartment and the reference compartment are provided with such gas permeable lining means for purpose of symmetry.

Accordingly, the present invention further provides an optical cell for use in a grating interferometer in which a laser beam is divided into a measuring beam and a reference beam travelling along respective optical paths extending in close parallel relationship over predetermined optical path lengths, which cell comprises a body formed with two elongated bores extending through the body in close parallel relation with one another to define elongated measuring and reference compartments for receiving respectively the measuring beam and reference beam therethrough, each compartment being provided with gas inlet and outlet means in gas flow communication with gas permeable lining means extending longitudinally of the compartment over the whole length thereof, the gas permeable lining means allowing uniform gas distribution or evacuation over substantially the whole compartment length.

Preferably, each compartment has a cylindrical cross-section which is constant from end to end and the gas permeable lining means comprise a plurality of tubular lining elements of similar wall thickness arranged coaxially in abutting engagement with one another to define an unsealed joint between two adjacent lining elements whereby to permit the aforesaid uniform gas distribution or evacuation. These lining elements may be removably inserted inside each compartment and held in place by window means at the ends of each compartment, the window means sealingly engaging outermost lining elements and being transparent to the measuring beam and reference beam for allowing passage of same therethrough, releasable retaining means being provided for releasably retaining the window means in sealing engagement with the outermost lining elements.

Turning to the mathematical development which has led to the present invention, the compressibility factor defined in equation (2) may be written as $$Z = P/\rho RT \quad (5)$$

where $\rho$ is the molar density. The invention is based on determining $\rho$ from the Lorentz-Lorenz equation $$\frac{n^2 - 1}{n^2 + 2} \cdot \frac{1}{\rho} = A_n + B_n\rho + C_n\rho^2 + \ldots \quad (6)$$

where n is the refractive index and $A_n$, $B_n$ and $C_n$ are respectively the first, the second and the third refractivity virial coefficients. Equation (6) can also be written as $$L_n = \frac{n^2 - 1}{n^2 + 2} = A_n\rho + B_n\rho^2 + C_n\rho^3 + \ldots \quad (7)$$

The first approximation for the density is given by $$\rho_1 = (L_n/A_n) \quad (8)$$

With this value of density one gets the first approximation for the compressibility factor $$Z_1 = (P/RT)(A_n/L_n)$$

The second approximation for $\rho$ is given by $$\rho_2 = (L_n n/A_n) - (B_n/A_n)(L_n/A_n)^2 \quad (10)$$

Replacing equation (10) in equation (5) one gets for the compressibility factor $$Z_2 = (P/RT)[(A_n/L_n) + (B_n/A_n)] \quad (11)$$

The third approximation for density given by $$\rho_3 = \frac{L_n}{A_n} - \frac{B_n}{A_n}\left(\frac{L_n}{A_n}\right)^2 + \frac{2B_n^2 - A_n C_n}{A_n^2}\left(\frac{L_n}{A_n}\right)^3 \quad (12)$$

leads to $$Z_3 = \frac{P}{RT}\left[\frac{A_n}{L_n} + \frac{B_n}{A_n} + \frac{C_n L_n}{A_n^2} - \frac{B_n^2 L_n}{A_n^3}\right] \quad (13)$$

where $Z_3$ is the compressibility factor incorporating the first three coefficients, $A_n$, $B_n$ and $C_n$, of the Lorentz-Lorenz equation.

Absolute refractive indices are calculated from laboratory measurements using the refractive index interferometer coupled to the pressure interferometer, by means of the formula:

$$n = (K\lambda/l) + 1 \quad (14)$$

where K is the total fringe count with reference to vacuum for a given pressure, $\lambda$ is the vacuum wavelength of light and l is the length of the measuring compartment of the optical cell of the refractive index interferometer, which is connected to the measuring compartment of the single cell of the pressure interferometer via the pressure equilibrium chamber.

The first refractivity virial coefficient $A_n$ is obtained by making an absolute measurement of the refractive index n as a function of pressure P. Expressing $\rho$ in terms of P as in equation (6), one gets $$[(n^2 - 1)/(n^2 + 2)][RT/P] = A_n + (B_n - A_n B_p)(P/RT) \quad (15)$$

where $B_p$, the second pressure virial coefficient, is given by the expansion $$(P/RT) = \rho + B_p\rho^2 + \ldots \quad (16)$$

When one plots the left side of equation (15) against P/RT, one can determine $A_n$ from the intercept. Although $B_n$ appears in the second term, this absolute method cannot be used for a precision determination of $B_n$ Since $B_n$ is a small fraction of the second term in equation (15), an error as small as 2% in $(B_n - A_n B_p)$ could lead to an error as large as 100% in $B_n$. In the present invention, $B_n$ is determined directly by using an expansion technique whereby the gas sample contained in the measuring compartment of one of the optical cells of the refractive index interferometer is expanded into the measuring compartment of the other cell of the refractive index interferometer.

The expansion technique is based on measuring the sum of optical path lengths of two similar compartments where one of them is filled with the gas sample at density p and the other is evacuated. After expansion, the density is nearly halved and one measures again the optical path lengths. Because the linear term in density remains the same before and after the expansion and only the quadratic and higher orders change, one can determine $B_n$ and $C_n$ from the change of the optical path lengths.

The development of $(n-1) \rho^{-1}$ as a function of density is given by $$(n-1)\rho^{-1} = A_m + B_m\rho + C_m\rho^2 + \ldots \quad (17)$$

The coefficients of equation (17) are related to those of equation (6) through the following relations:

$$A_n = (\tfrac{2}{3})A_m \quad (18)$$

$$B_n = (\tfrac{2}{3})B_m - (1/9)A_m^2 \quad (19)$$

$$C_n = (\tfrac{2}{3})C_m - (2/9)A_m B_m - (4/27)A_m^3 \quad (20)$$

Considering the measuring compartments of both cells of the refractive index interferometer as having respectively volumes A and B given by $V_A = V(1+\delta)$ and $V_B = V(1-\delta)$ where $\delta$ is small and the optical path length of each volume as being given by $l_A = l(1+\Delta)$ and $l_B = l(1-\Delta)$, where $\Delta$ is also small, if A initially contains a gas of refractive index $n_A$, at a density $\rho_A$ while B is evacuated, one observes a change ($D_A$) of refractive index on expansion from A and B. $D_A$ is defined by the relation $$D_A = (n_A - 1)(1 + \Delta) - 2(n_{AB} - 1) \quad (21)$$

where $n_{AB}$ is the refractive index of the gas in both volumes after the expansion. One then gets $$D_A = A_m(\Delta - \delta)\rho_A + \frac{B_m}{2}[1 + 2(\Delta - \delta)]\rho_A^2 + \quad (22)$$

$$\frac{C_m}{4}[3 + (4\Delta - 3\delta)]\rho_A^3 + \ldots$$

Similarly, if B contains a gas with refractive index $n_B$ and density $\rho_B$ and if A is evacuated, the expansion from B to A leads to a corresponding change $D_B$ in the index of refraction. $D_B$, defined in the same way as $D_A$, is given by $$D_B = -A_m(\Delta - \delta)\rho_B + \frac{B_m}{2}[1 - 2(\Delta - \delta)]\rho_B^2 + \quad (23)$$

$$\frac{C_m}{4}[3 - (4\Delta - 3\delta)]\rho_B^3 + \ldots$$

From equation (17), $\rho_A$ and $\rho_B$ can be expressed in terms of $n_A - 1$ and $n_B - 1$ as $$\rho_A = (n_A - 1)/A_m - (n_A - 1)^2 B_m/A_m^3 + (n_A - 1)^3 \quad (24)$$

$$[(2B_m^2 - A_m C_m)/A_m^5] + \ldots$$

$$\rho_B = (n_B - 1)/A_m - (n_B - 1)^2 B_m/A_m^3 + (n_B - 1)^3 \quad (25)$$

$$[(2B_m^2 - A_m C_m)/A_m^5] + \ldots$$

On replacing $\rho_A$ and $\rho_B$ in equations (22) and (23) by equations (24) and (25), one gets by combining equations (22) and (23):

$$D_A/(n_A - 1) + D_B/(n_B - 1) = \quad (26)$$

$$(B_m/2A_m^2)[(n_A - 1) + (n_B - 1)] +$$

$$((3A_m C_m - 4B_m^2)/4A_m^4)[(n_A - 2)^2 + (n_B - 1)^2]$$

With the help of equation (14), one can transform equation (26) in a more convenient form, given by the function $$F = (\Delta K_{AB})/K_A + (\Delta K_{BA})/K_B = [B_m/(2A_m^2)](\lambda/l)[K_A + K_B] + \quad (27)$$

$$((3A_m C_m - 4B_m^2)4A_m^4)(\lambda/l)^2[K_a^2 + K_B^2] + \ldots$$

where $K_A$ and $K_B$ correspond to absolute number of fringes in A and B before expansion; $\Delta K_{AB}$ and $\Delta K_{BA}$ are respectively the number of fringes observed after the expansion from A to B and from B to A, once the thermodynamic equilibrium has been reached. The measurements are carried out in such a way that $K_A$ is nearly equal to $K_B$. The variable in the second term, $K_A^2 + K_B^2$, can then be written as $(K_A + K_B)^2/2$.

On plotting F against $(K_A + K_B)$, one gets $B_n$ and $C_n$ from a least squares fit of a polynomial of the $$y = ax + bx^2 + cx^3 + \ldots \quad (28)$$

The errors in the function F decrease with pressure and hence the higher pressure measurements are weighted more.

From equation (13), one can see that the uncertainty in the compressibility factor $Z_3$ is due to uncertainties in P, R, T, $L_n$, $A_n$, $B_n$ and $C_n$. It should be pointed out that, generally, 99% of the contribution in $Z_3$ comes from the first term $Z_1 = (P/RT)(A_n/L_n)$. The remaining contribution of about 1% comes from terms involving $B_n$ and $C_n$. In the first term, the experimental error in $L_n/P$ is due to systematic errors such as the length of the cell, calibration of the pressure interferometer, gas purity, etc., as well as random error of the fringe counts. However, to a great extent, the systematic error in $L_n/P$ is not transferred to Z, if the compressibility factor is calculated by using the same $L_n/P$ data that is used to determine $A_n$. One has $$A_n = RT \lim (L_n/P) \ldots L_n, P \to 0 \quad (29)$$

and $$Z_1 = (P/RT)(A_n/L_n) = (L_n/P)^{-1} \lim (L_n/P) \ldots L_n, P \to 0 \quad (30)$$

This partial error compensation in the data reduction causes the uncertainty in $Z_1$ to be dominated by the random error in the fringe counts which is in the order of $\pm 10^{-4}$ at 10 bars and $\pm 10^{-5}$ at 300 bars. order of at 300 bars.

Experimental error in the expansion experiments gives rise to uncertainties in $B_n$ and $C_n$. An observed uncertainty of 3% in $B_n$ and $C_n$ leads to uncertainties of the order of $3 \cdot 10^{-4}$ and $2 \cdot 10^{-4}$ in $Z_3$ of methane at 300 bars.

The uncertainties in $Z_3$ due to temperature T and the universal gas constant R are respectively $3 \cdot 10^{-5}$ and $1 \cdot 10^{-4}$.

The errors arising from the effect of adsorption is not important in the present invention. Since the absolute value of the refractive index depends only on the density in the gas phase, the first term in $Z_3$ is not affected by adsorption. The adsorption in the expansion experiment to determine $B_n$ and $C_n$ is to a large extent also cancelled if one assumes a linear variation of adsorption with pressure.

BRIEF DESCRIPTION OF THE DRAWINGS

Further features and advantages of the present invention will become more readily apparent from the following description of preferred embodiments with reference to the appended drawings, in which.

DESCRIPTION OF PREFERRED EMBODIMENTS

Figure 1:
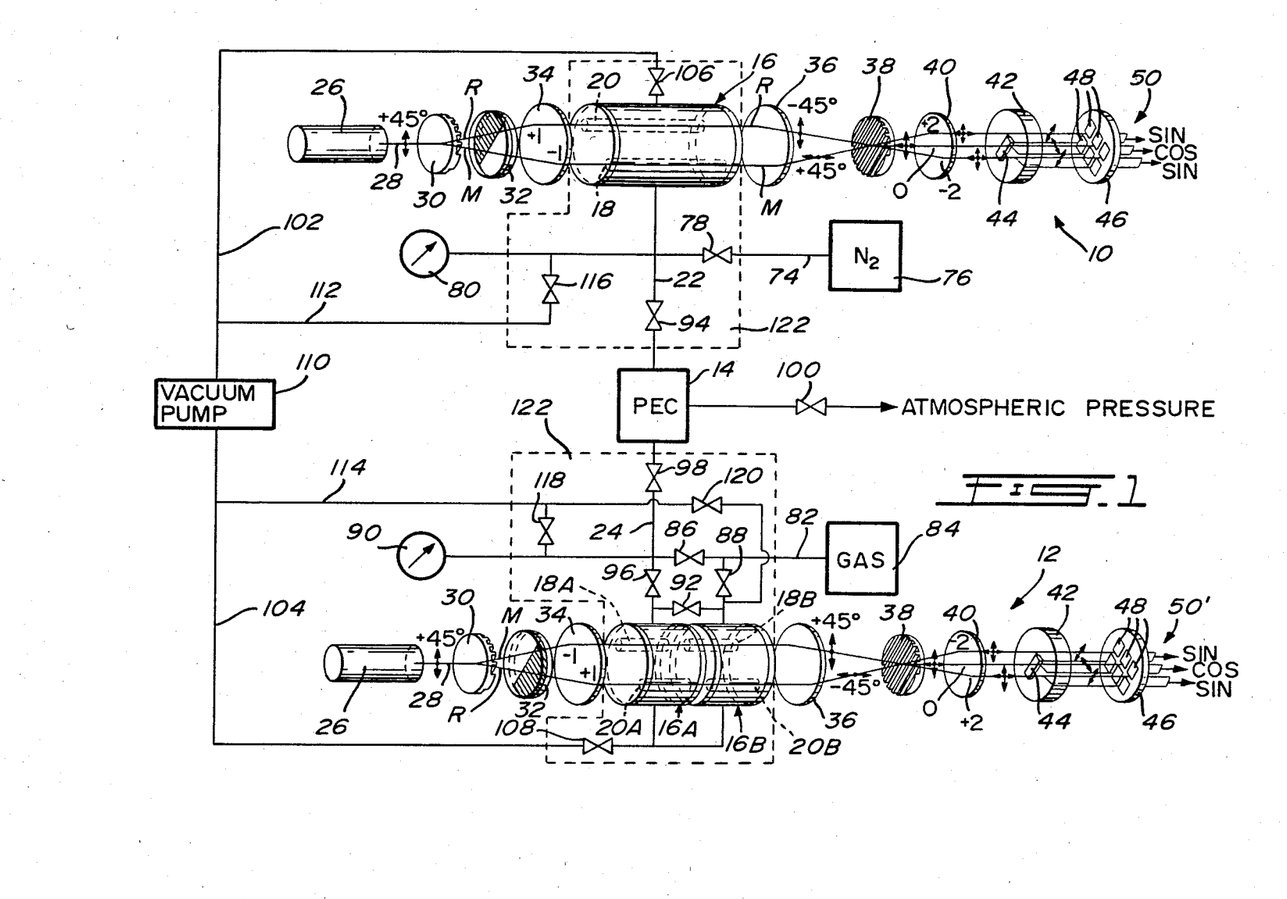
FIG. 1 is a schematic perspective view of an apparatus according to the invention.

Referring first to FIG. 1, there is shown an apparatus for the precise determination of the compressibility factor of a gas sample, comprising three main components, namely two grating interferometers 10 and 12 defining respectively a pressure interferometer and a refractive index interferometer, and a pressure equilibrium chamber (PEC) 14 coupling both interferometers. The advantage of using a grating interferometer is that it enables to perform a reversible counting and to generate a d.c. compensated signal from the interference fringes.

Accurate determination of the compressibility factor involves precise measurements of $L_n$, P, T, $A_n$, $B_n$ and $C_n$ in equation (13). Measuring the pressure at the same time as the refractive index increases the efficiency of data taking. The provision of a pressure interferometer coupled with a refractive index interferometer enables the pressure to be measured as fast as the refractive index.

The interferometer 10 used for the pressure measurement is of the same type as the refractive index interferometer 12 and was previously calibrated by Physikalisch-Technische Bundesanstalt (PTB), Braunschweig, Federal Republic of Germany, with an oil type precision piston gauge. Nitrogen of exceptionally high purity (99.9995%) is used for the calibration as a measuring gas for the pressure interferometer because of its suitable physical properties. Since only sixteen pressure values are given by PTB and are uncertain to the order of $5 \cdot 10^{-5}$, a least square fit polynomial for the pressure values in terms of the number of fringes was developed for the purpose of calibration at any given point. This, of course, increased the uncertainty of pressure measurement for pressures above 10 bars to $8 \cdot 10^{-5}$. Small errors due to temperature and the purity of nitrogen gas were also considered. The final uncertainty from all these errors was $1 \cdot 10^{-4}$ for pressures above 10 bars.

The pressure interferometer 10 comprises a single optical cell 16 whereas the refractive index interferometer 12 comprises two optical cells 16A and 16B in tandem alignment, the cells 16, 16A and 16B being essentially of the same construction and each including elongated measuring and reference compartments 18,20, 18A,20A and 18B,20B, respectively. The measuring compartment 18 of cell 16 is connected to the measuring compartment 18A of cell 16A via the pressure equilibrium chamber 14 by means of the valved conduits 22 and 24. This arrangement enables the pressure to be maintained at the same value in the compartments 18 and 18A of cells 16 and 16A, and permits to carry out high speed measurements of pressure and refractive index which would otherwise be much reduced by the incorporation of a differential pressure indicator (DPI), commonly used for coupled measurements. As example of suitable pressure equilibrium chamber 14, use can be made of the differential pressure null cell and indicator sold under the trademark RUSKA.

As shown in FIG. 1, each interferometer comprises a He-Ne laser source 26 adapted to generate a monochromatic laser beam 28 linearly polarized at 45°. The laser beam 28 passes through a first grating 30, thereby producing numerous diffraction orders. Two symmetrical beams of the first diffraction orders (+1, −1) are selected such that one of them acts as a measuring beam M and the other as a reference beam R and both have sufficient light intensity to be detected at a later stage. One of the beams passes through a half-wavelength plate 32 such that the measuring beam M and reference beam R have respective polarization planes which are perpendicular to one another. The two beams M and R are rendered parallel by the optical lens 34 and then enter the respective optical cells of the interferometers, where the measuring beam M and reference beam R pass respectively through the measuring compartment 18 and reference compartment 20 of the cell 16 in the case of the pressure interferometer 10, and through the measuring compartments 18A,18B and reference compartments 20A,20B of the cells 16A,16B in the case of the refractive index interferometer 12. A second optical lens 36 is used to thereafter focus the two beams M and R on a second grating 38. The planes of polarization of the beams M and R are not affected by the two gratings 30 and 38.

The measuring beam M and reference beam R focused on the second grating 38 produce two diffraction patterns superimposed on one another. The resultant diffraction pattern comprises several diffraction orders and only three superposed orders (0, ±2) are selected which have enough contrast to be converted to electrical signals at a later stage. The three beams corresponding to the selected orders of diffraction are rendered parallel by a third optical lens 40 and then caused to impinge on a double refracting quartz plate 42 with a quarter-wavelength plate 44 being incorporated in the optical path of the beam of the zero order of diffraction. The double refracting quartz plate 42 produces three pairs of phase modulated optical signals, each pair of optical signals being in-phase and anti-phase with one pair being in quadrature with the two other pairs. These optical signals are thereafter converted into corresponding push-pull modulated electrical signals (±sin, ±cos, ±sin) by means of a signal converter 46 comprising an array of six photodiodes 48 having very similar dependence on dark currents and temperature coefficients. The photodiodes 48 arranged in a matrix not only transform the optical signals into electrical signals but also simplify mechanical adjustments and shorten the amplifier connections used for processing the electrical signals. The signal of information 50 provided at the output of the pressure interferometer 10 is related to the pressure of the gas sample whereas the signal of information 50' provided at the output of the refractive index interferometer 12 is related to the refractive index of such a gas sample.

As previously indicated, the optical cells 16,16A and 16B are of similar construction, the cell 16 differing only in length from the cell 16A or 16B. Cells 16A and 16B have substantially the same lengths whereas cell 16 has a length about twice the length of cell 16A or 16B.

Figure 2:
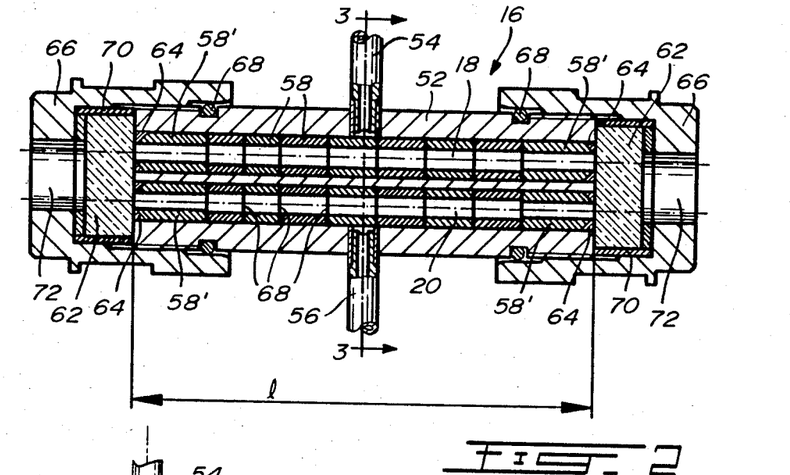
FIG. 2 is a longitudinal sectional view of an optical cell used in the apparatus of FIG. 1.
Figure 3:
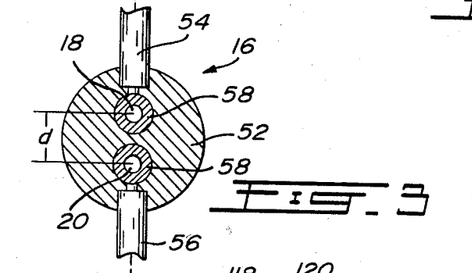
FIG. 3 is a section along line 3—3 of FIG. 2.

FIGS. 2 and 3 illustrate the construction of the above optical cells. As shown, the cell 16 has an elongated body 52 of circular cross-section, which is generally made of stainless steel. The body 52 typically has an external diameter of 30 mm and a length l of 100 mm. It is formed with two cylindrical bores each typically having a diameter of 8 mm, which extend through the body in close parallel relation with one another and are arranged symmetrically about the center axis of the body, whereby to define the aforesaid measuring compartment 18 and reference compartment 20 for receiving respectively the measuring beam and reference beam. The compartments 18 and 20 are respectively provided with gas inlet/outlet conduits 54 and 56 which are in gas flow communication with a plurality of tubular lining elements 58 of similar wall thickness arranged coaxially in abutting engagement with one another and extending over the whole length l of each compartment. These lining elements thus define a plurality of unsealed joints 60 allowing uniform gas distribution or evacuation over substantially the whole compartment length.

The lining elements 58 which each typically have an external diameter of 8 mm and an internal diameter of 3 mm, are removably inserted inside each compartment and are held in place by a quartz window 62 at each end of the body 52. The windows 62 sealingly engage the outermost lining elements 58′; to this end, the lining elements 58′ have chamfered ends for seating TEFLON (trademark) O-rings 64 which independently seal the measuring compartment 18 and the reference compartment 20. Two releasable end covers 66 which sealingly engage the ends of the body 52 by means of TEFLON O-rings 68 are provided for retaining the windows 62 in sealing engagement with the lining elements 58′. A TEFLON protector 70 in the form of a sleeve is arranged between each window 62 and cover 66. The covers 66 are each formed with a central aperture 72 for allowing passage of the measuring beam and reference beam through the windows 62 and the compartments 18 and 20.

The variation in length of the measuring compartment 18 due to change in pressure is compensated to a great extent by arranging the measuring compartment 18 and the reference compartment 20 very close to one another. As best shown in FIG. 3, the distance d between the compartments 18 and 20 is typically 10 mm. In other words, due to their closeness, both compartments undergo the same deformation under pressure so that the variation in length is at anytime the same in both.

The apparatus shown in FIG. 1 further includes a supply line 74 interconnecting a source 76 of high purity nitrogen with the measuring compartment 18 of the cell 16 via line 22. The line 74 is provided with a supply valve 78 and a pressure gauge 80. Another supply line 82 interconnects a source 84 of the gas under test with the measuring compartments 18A,18B of the cells 16A,16B, the line 82 being provided with supply valves 86 and 88 and a pressure gauge 90. The compartments 18A and 18B of the cells 16A and 16B are interconnected by means of an expansion valve 92. The lines 22 and 24 which connect the measuring compartment 18 of the cell 16 to the measuring compartment 18A of the cell 16A via the pressure equilibrium chamler 14 are provided respectively with valves 94 and 96, the line 24 being provided with an additional valve 98 for selectively coupling or uncoupling the interferometers 10 and 12. The pressure equilibrium chamber 14, on the other hand, is provided with an exhaust valve 100 for venting to the atmosphere. Two vacuum lines 102 and 104 provided respectively with valves 106 and 108 interconnect a mechanical vacuum pump 110 with the reference compartments 20,20A,20B of the cells 16,16A,16B for maintaining same substantially under vacuum. Two additional vacuum lines 112 and 114 connected to the vacuum pump 110 and having valves 116, 118 and 120 are provided for evacuating the measuring compartments 18,18A,18B of the cells 16,16A,16B. All the cells and valves with the exception of valve 100 are immersed in a thermostatic bath 122 represented in broken lines, for maintaining the same at a constant temperature.

Figure 6:
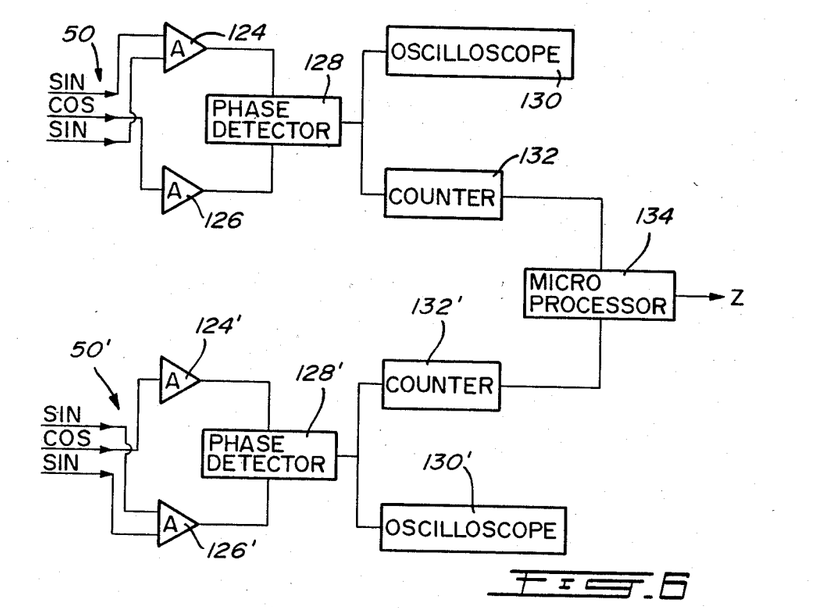
FIG. 6 is a schematic diagram of the electronic circuit used for processing the output signals shown in FIG. 1.

Turning to FIG. 6 which schematically illustrates the circuit used for processing the output signals 50 and 50′ of the pressure interferometer 10 and refractive index interferometer 12, the two sine signals provided by the interferometer 10 are introduced into the inputs of a first differential amplifier 124 where they are combined in such a way that the d.c. parts of the signals are compensated. The cosine signal is introduced into the input of a second differential 126. The amplitude of the cosine signal is approximately equal to the sum of the amplitudes of the two sine signals. The outputs of the amplifiers 124 and 126 are connected to a phase detector 128 whereby to produce a d.c. compensated rotating electrical field at the output of the detector 128. This rotating electrical field which can be visualized on an oscilloscope 130 connected to the detector 128 operates a reversible counter 132 which is also connected to the detector 128 and digitizes each change of one wavelength into 256 parts. One full rotation of the electrical field corresponds to an optical change of one wavelength and thus to one fringe count.

The signal of information 50′ provided by the refractive index interferometer 12 is treated in exactly the same way by means of the differential amplifiers 124′ and 126′, phase detector 128′ and reversible counter 132′, the oscilloscope 130′ being provided for visualizing the rotating electrical field at the output of the detector 128′. The fringe counts associated with each interferometer and provided by the counters 132 and 132′ are then fed to a micro-processor 134 which processes the data together with the temperature value of the thermostatic bath 122 (FIG. 1) to obtain the compressibility factor Z.

The operation of the apparatus shown in FIG. 1 for the determination of the compressibility factor of the gas sample contained in source 84 is as follows.

Figure 4:
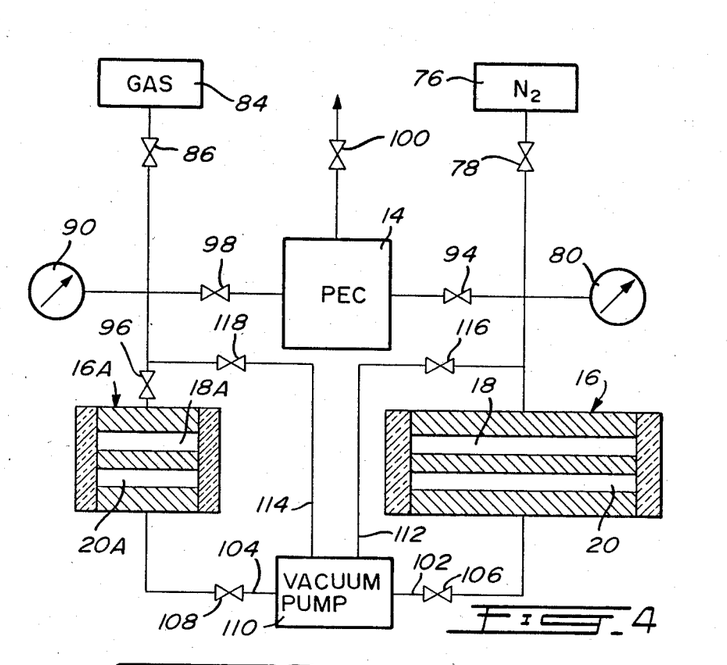
FIG. 4 is a schematic sectional view of the measuring and pressure cells of the refractive index interferometer and pressure interferometer, respectively, showing how they are coupled.

The terms $L_n$ and $A_n$ in equation (13) are first determined using the cells 16 and 16A of the interferometers 10 and 12 in their coupled mode, as best shown in FIG. 4. The pressure interferometer 10 and the refractive index interferometer 12 are coupled together by opening valve 98. The pressure equilibrium chamber 14 as well as the measuring compartments 18 and 18A of the cells 16 and 16A are evacuated by opening valves 94, 96, 116 and 118. Once the chamber 14 and the compartments 18 and 18A are evacuated, the valves 94, 98, 116 and 118 are closed whereas the valve 96 is left open. The reference compartments 20 and 20A, on the other hand, are maintained under vacuum by leaving valves 106 and 108 open. The supply valve 78 is then opened to allow the nitrogen from the source 76 to fill the compartment 18 at a pressure $P_1$, e.g. 300 bars. The supply valve 86 is in turn opened to allow the gas sample from the source 84 to fill the compartment 18A at a pressure $P_2$ such that $P_2 \simeq P_1$ by observing the bourdon-type gauges 80 and 90, thereby obtaining rough equilibrium pressures in the compartments 18 and 18A. The valves 78 and 86 are closed and the valves 94 and 98 are slowly opened at the same time in order to fill the pressure equilibrium chamber 14. A null pressure difference must be maintained on both sides of the pressure equilibrium chamber 14 until the equilibrium in pressure is established in the chamber 14 and the compartments 18 and 18A. The valve 98 is thereafter closed. The valve 94 is fully opened and the exhaust valve 100 is only partially opened to observe on the oscilloscope 130 (FIG. 6) the direction of rotation of the electrical field produced by the pressure interferometer 10. The valve 98 is very carefully opened to similarly observe on the oscilloscope 130' (FIG. 6) the direction of rotation of the electrical field produced by the refractive index interferometer 12. If the two rotating electrical fields observed on the oscilloscopes 130 and 130' move in the same direction, then pressure equilibrium is obtained in the pressure equilibrium chamber 14. If the rotating electrical fields move in opposite directions, valve 98 is closed since $P_1 > P_2$; valve 100 is left partially opened to lower the pressure $P_1$ and valve 98 is again very carefully opened to observe the direction of rotation of the electrical field on the oscilloscope 130'. When the two rotating electrical fields on the oscilloscopes 130 and 130' move in the same direction, valve 98 can be opened completely. The exhaust valve 100 is then closed and the recording of the fringe counts provided by both interferometers is taken only when the thermodynamic equilibrium is reached in the pressure equilibrium chamber 14; the thermodynamic equilibrium can be ascertained by observing the stability of counters 132 and 132', or of the electrical fields on the oscilloscopes 130 and 130' (FIG. 6).

Figure 7:
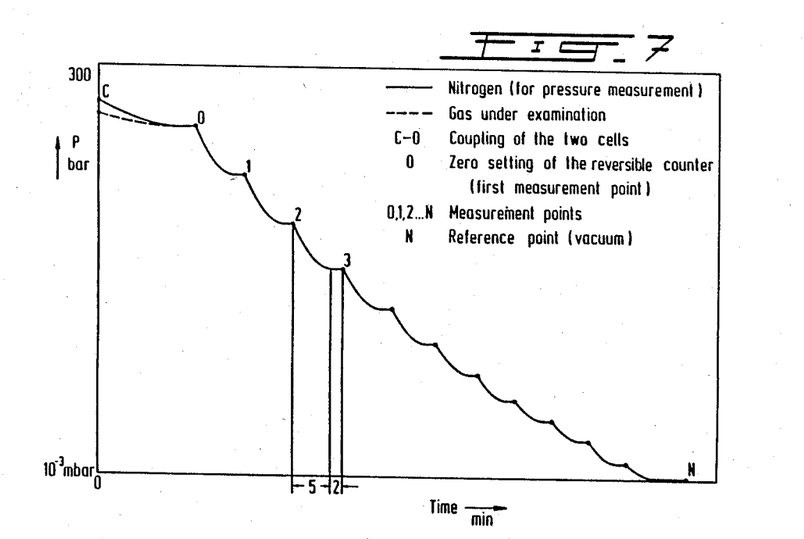
FIG. 7 is a plot of the pressure as a function of time for both the refractive index interferometer and the pressure interferometer when coupled together.

The fringe counting starts at the point "0" as illustrated in FIG. 7. Further pressure changes and data collecting are carried out by only manipulating valve 100 so as to stepwise lower the pressure of the nitrogen and gas sample in the compartments 18 and 18A, the fringe counts provided at each step by both interferometers being recorded once the thermodynamic equilibrium has been re-established. When the pressure of the nitrogen and gas sample has reached atmospheric pressure, the discard valve 100 is closed and valves 116 and 118 are manipulated in the same way as valve 100 so as to further stepwise lower the pressure of the nitrogen and gas sample until substantially vacuum is attained in the compartments 18 and 18A. Two sets of data are thereby obtained, one being related to the pressure (P) of the gas sample and the other to the refractive index (n) thereof as a function of pressure.

The possible mixing of nitrogen with the gas sample by diffusion between the compartments 18 and 18A when the valve 100 is closed is avoided by using long conduits of small internal diameter (about 1 mm). Since the duration of the time when valve 100 is closed is only a small fraction (about 4–5 minutes) of the total time of the experiment (about 3–4 hours), the problem of diffusion is certainly negligible.

The absolute refractive index is obtained by counting the changes in the interference fringes while venting the nitrogen and gas sample to the atmosphere and then to vacuum. Final vacuum in the measuring compartments 18 and 18A of both cells 16 and 16A is necessary because interferometric measurements of the refractive index must be made relative to the vacuum.

Figure 8:
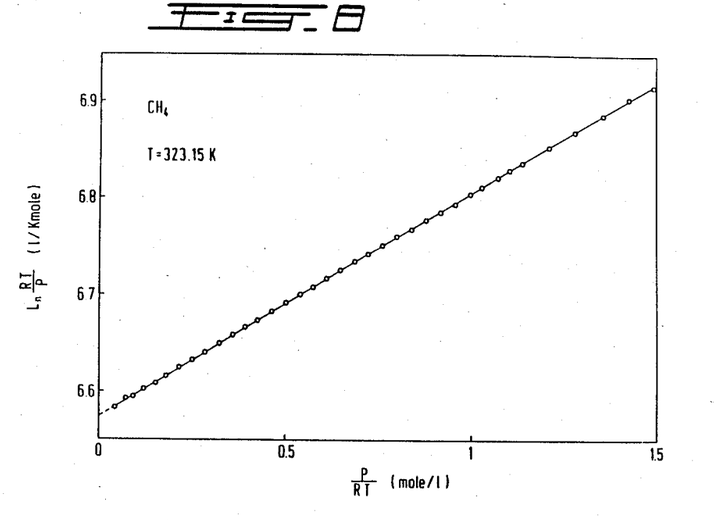
FIG. 8 which is on the same sheet of drawings as FIG. 4 represents the Lorentz-Lorenz function of $CH_4$ plotted as a function of P/RT at 323.15° K.

The absolute refractive index (n) of the gas sample is calculated from the data provided by the refractive index interferometer 12 by means of equation (14). The refractive index n in turn is used to calculate the term $L_n$ in equation (13), by means of equation (7). The first refractivity virial coefficient $A_n$, on the other hand, is obtained by plotting $L_n RT/P$ against $P/RT$ and determining $A_n$ from the intercept. An example of such a plot for methane at 323.15° K. is represented in FIG. 8, where the points are experimental and the curve is a least-squares fit.

Figure 5:
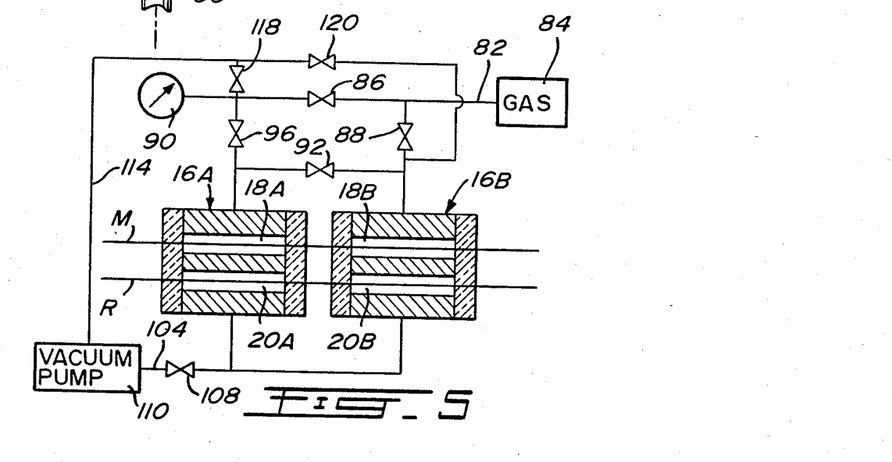
FIG. 5 which is on the same sheet of drawings as FIGS. 2 and 3 is another schematic sectional view of both cells of the refractive index interferometer, showing their interconnection.

The second and third refractivity virial coefficients $B_n$ and $C_n$ in equation (13) are determined by means of an expansion technique, using only the refractive index interferometer 12. To this end, the pressure interferometer 10 and refractive index interferometer 12 are uncoupled one from another by closing the valve 98. As best shown in FIG. 5, the measuring compartment 18B of the cell 16B is evacuated by opening valve 120; the reference compartments 20A and 20B of the cells 16A and 16B are still maintained under vacuum by leaving valve 108 open. Once the compartment 18B is evacuated, the valve 120 is closed. Valves 86 and 96 are then slowly opened to allow the gas sample from the source 84 to fill the compartment 18A at a predetermined pressure above atmospheric pressure, e.g. 150 bars. The valves 86 and 96 are thereafter closed and the gas sample in the compartment 18A is allowed to reach thermodynamic equilibrium, which can be ascertained by observing on the oscilloscope 130' (FIG. 6) the stability of the rotating electrical field produced by the interferometer 12. The number of fringes $K_A$ provided by the interferometer before expansion is recorded. The expansion valve 92 is then very slowly opened so as to cause the gas sample to expand from the compartment 18A into the compartment 18B and to thus fill both compartments; since the compartments 18A and 18B have the same volume and also the same length, the density of the gas sample is halved. Once the thermodynamic equilibrium has been re-established, the valve 92 is closed and after the thermodynamic equilibrium has re-established once again the number of fringes $\Delta K_{AB}$ provided by the interferometer is recorded.

Thereafter, both compartments 18A and 18B are evacuated by opening valves 96, 118 and 120. The above expansion technique is then repeated but from compartment 18B towards compartment 18A, that is, in an inverse direction from the above, in order to compensate from small differences in volume and length between the measuring compartments 18A and 18B. To this end, the valves 96, 118 and 120 are closed and the valve 88 is slowly opened to allow the gas sample from the source 84 to fill the compartment 18B at the same pressure as above, the pressure being verified by means of the bourdon-type gauge 90 (valve 86 being opened). Valve 88 is closed and the number of fringes $K_B$ provided by the interferometer is recorded once the gas sample in compartment 18B has reached thermodynamic equilibrium. The expansion valve 92 is then very slowly opened so as to cause the gas sample to expand from the compartment 18B into the compartment 18A and to thus fill both compartments as before. Once the thermodynamic equilibrium has been re-established, the valve 92 is closed and after the thermodynamic equilibrium has been re-established once again the number of fringes $\Delta K_{BA}$ provided by the interferometer is recorded.

Figure 9:
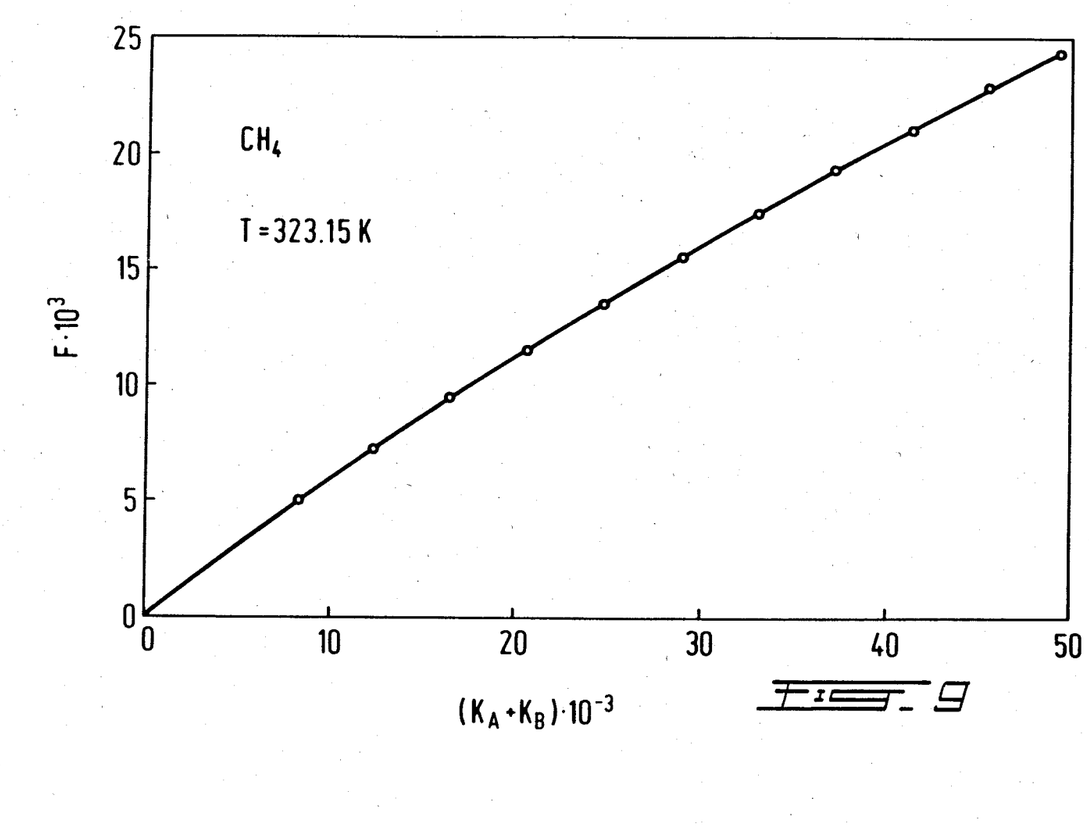
FIG. 9 is a plot of the refractive index expansion function F against KA+KB.

The above two expansion procedures, that is, from compartment 18A to compartment 18B and then from compartment 18B to compartment 18A, are repeated several times as paired steps with each of the paired steps being carried out at a different pressure above atmospheric pressure, to obtain sufficient data for plotting the refractive index expansion function F of equation (27) against $(K_A + K_B)$. An example of such a plot for methane at 323.15° K. is represented in FIG. 9, where the points are experimental and the curve is a least-squares fit. The coefficients $B_n$ and $C_n$ can thus be determined respectively from the slope at the origin and the curvature of such curve.

Figure 10:
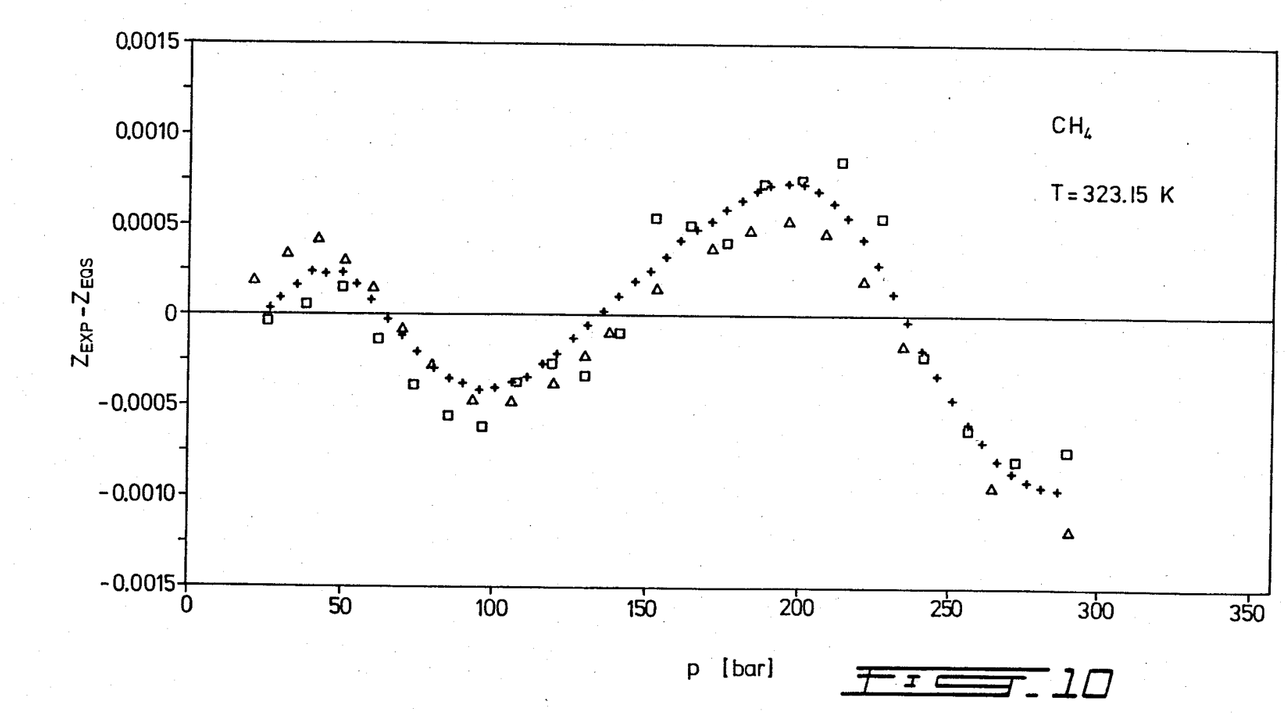
FIG. 10 is a diagram illustrating the deviations of different experimental values of the compressibility factor $Z_{exp}$ from $Z_{eqs}$ values calculated using the Goodwin equation of state as reference.

FIG. 10 illustrates the deviations of the experimental values of the compressibility factor $Z_{exp}$ obtained with the apparatus of FIG. 1 and represented by the symbol (+), from $Z_{eqs}$ values calculated using the Goodwin equation of state as reference (R.D. Goodwin, Natl, Bur. Stand. (U.S.), Tech. Note 653 (1974)). In FIG. 10, the symbols (□) and (Δ) represent experimental values obtained respectively by Douslin et al. (J. Chem. Eng. Data, Vol. 9, p. 358 (1964)) and Trappeniers et al. (Physica, Vol. 98A, p. 289 (1979)).

As it is apparent, the method according to the invention which is based on combining the aforementioned expansion technique with the absolute measurements of the refractive index as a function of pressure leads to values of the compressibility factor comparable to the best PVT values. The method of the invention is not only precise for the determination of the compressibility factor but also has the ability of producing numerous experimental points in a much sorter time (generally less than 24 hours) as compared to other methods.

We claim:

1. A method for the precise determination of the compressibility factor of a gas sample, wherein use is made of two grating interferometers coupled together with one interferometer defining a refractive index interferometer adapted to provide a signal of information related to the refractive index of said gas sample and the other interferometer defining a pressure interferometer adapted to provide another signal of information related to the pressure of said gas sample whereby to permit measurement of the refractive index as a function of pressure, each interferometer being capable of dividing a linearly polarized monochromatic laser beam into a measuring beam and a reference beam and causing said measuring beam and reference beam to travel along respective optical paths extending in close parallel relationship over predetermined optical path lengths, said refractive index interferometer and pressure interferometer comprising respectively two optical cells in tandem alignment and a single optical cell with each cell having elongated measuring and reference compartments arranged in close parallel relationship along the parallel optical paths of said measuring beam and reference beam to receive same therethrough, the measuring compartments of both cells of said refractive index interferometer being interconnected to permit gas expansion therebetween with the measuring compartment of one of said cells being connected to the measuring compartment of said single cell of said pressure interferometer via a pressure equilibrium chamber to provide said interferometer coupling, said method comprising the steps of:

(a) maintaining all said optical cells at a constant predetermined temperature value;

(b) filling the measuring compartments of said one cell and said single cell respectively with said gas sample and a selected gas at a same pressure above atmospheric pressure and allowing said gas sample and selected gas to reach thermodynamic equilibrium in said pressure equilibrium chamber;

(c) stepwise lowering the pressure of said gas sample and selected gas until substantially vacuum is attained in the measuring compartments of both said one cell and said single cell while maintaining the reference compartments thereof substantially under vacuum and recording at each step the signals of information provided by both interferometers once the thermodynamic equilibrium has been re-established in said pressure equilibrium chamber, thereby obtaining first and second sets of data;

(d) uncoupling said refractive index interferometer and pressure interferometer from one another;

(e) evacuating the measuring compartment of the other cell of said refractive index interferometer, re-filling the measuring compartment of said one cell with said gas sample at superatmospheric pressure, allowing said gas sample to reach thermodynamic equilibrium. recording the signal of information provided by said refractive index interferometer, causing said gas sample to expand into the measuring compartment of said other cell while maintaining the reference compartments of both said one cell and said other cell substantially under vacuum, and recording again the signal of information provided by said refractive index interferometer once the thermodynamic equilibrium of said gas sample has been re-established;

(f) evacuating the measuring compartments of both said one cell and said other cell, filling the measuring compartment of said other cell with said gas sample at a pressure equal to said surperatmospheric pressure of step (e), allowing said gas sample to reach thermodynamic equilibrium, recording the signal of information provided by said refractive index interferometer, causing said gas sample to expand into the measuring compartment of said one cell while still maintaining the reference compartments of both said one cell and said other cell substantially under vacuum, and recording again the signal of information provided by said refractive index interferometer once the thermodynamic equilibrium of said gas sample has been re-established;

(g) repeating steps (e) and (f) several times as paired steps after evacuation of the measuring compartment of said one cell, each of said paired steps being carried out at a different pressure above atmospheric pressure, thereby obtaining a third set of data; and (h) processing said first, second and third sets of data obtained in steps (c) and (g) together with the temperature value of step (a) through circuitry means to obtain the compressibility factor of said gas sample.

2. A method as claimed in claim 1, wherein said selected gas is nitrogen of at least research grade purity.

3. A method as claimed in claim 1, wherein the temperature value in step (a) is selected from the range of about 0° to about 100° C.

4. A method as claimed in claim 1, wherein the pressure of said gas sample and selected gas in step (b) is in the range of about 100 to about 500 bars.

5. A method as claimed in claim 1, wherein the pressure of said gas sample in steps (e) and (f) is selected from the range of about 50 to about 500 bars and said steps (e) and (f) are repeated at pressures above said selected pressure.

6. A method as claimed in claim 1, wherein the pressure of said gas sample in steps (e) and (f) is selected from the range of about 50 to about 500 bars and said steps (e) and (f) are repeated at pressures below said selected pressure.

7. A method as claimed in claim 1, wherein after expansion in step (e) or (f) said gas sample has a density reduced substantially by half.

8. A method as claimed in claim 1, wherein the laser beam of each interferometer is a He-Ne laser beam polarized at 45° and the reference beam issued from said laser beam is passed through a half-wavelength plate such that said measuring beam and reference beam have respective polarization planes which are perpendicular to one another.

9. A method as claimed in claim 8, wherein the measuring beam and reference beam of each interferometer after having travelled said predetermined optical path lengths are focussed on a grating to produce three beams corresponding to selected superposed diffraction orders including a zero order of diffraction, said three beams are rendered parallel and caused to impinge on a double refracting quartz plate with a quarter-wavelength plate being incorporated in the optical path of the beam of the zero order of diffraction to produce three pairs of phase modulated optical signals, each pair of optical signals being in-phase and anti-phase with one pair being in quadrature with the other two pairs, and said optical signals are converted into corresponding push-pull modulated electrical signals which are processed electronically to produce a d.c. compensated rotating electrical field associated with each interferometer, and wherein the thermodynamic equilibrium of said gas sample in steps (b), (c), (e) and (f) and of said selected gas in steps (b) and (c) is ascertained by observing the stability of the electrical fields associated respectively with said refractive index interferometer and said pressure interferometer.

10. An apparatus for the precise determination of the compressibility factor of a gas sample, comprising two grating interferometers coupled together with one interferometer defining a refractive index interferometer adapted to provide a signal of information related to the refractive index of said gas sample and the other interferometer defining a pressure interferometer adapted to provide another signal of information related to the pressure of said gas sample whereby to permit measurement of the refractive index as a function of pressure, each interferometer including means for dividing a linearly polarized monochromatic laser beam into a measuring beam and a reference beam and means for causing said measuring beam and reference beam to travel along respective optical paths extending in close parallel relationship over predetermined optical path lengths, said refractive index interferometer and pressure interferometer comprising respectively two optical cells in tandem alignment and a single optical cell with each cell having elongated measuring and reference compartments arranged in close parallel relationship along the parallel optical paths of said measuring beam and reference beam to receive same therethrough, said apparatus further including means for maintaining all said optical cells at a constant predetermined temperature value, first valved conduit means connecting the measuring compartment of one of said cells of said refractive index interferometer with the measuring compartment of said single cell of said pressure interferometer via a pressure equilibrium chamber to selectively couple or uncouple said interferometers, second valved conduit means interconnecting both cells of said refractive index interferometer to permit gas expansion therebetween when said interferometers are uncoupled and thereby enable said refractive index interferometer to provide a further signal of information, third valved conduit means adapted to connect a vacuum means to the reference compartments of all said cells for maintaining same substantially under vacuum and to the measuring compartments of both cells of said refractive index interferometer for evacuating same after said gas expansion, fourth valved conduit means adapted to connect a source of said gas sample to the measuring compartments of both cells of said refractive index interferometer for filling the measuring compartment of either cell with said gas sample at superatmospheric pressure, fifth valved conduit means adapted to connect a source of a selected gas to the measuring compartment of said single cell of said pressure interferometer for filling same with said selected gas at superatmospheric pressure, said first and third valved conduit means being operative to stepwise lowering the pressure of said gas sample and selected gas until substantially vacuum is attained in the measuring compartments of both said one cell and said single cell when said interferometers are coupled, and circuitry means for processing the signals of information provided by both interferometers as a result of said pressure lowering and said gas expansion together with said temperature value to obtain the compressibility factor of said gas sample.

11. An apparatus as claimed in claim 10, wherein the measuring compartments of both cells of said refractive index interferometer have substantially equal volumes, and the measuring compartment of said single cell of said pressure interferometer has a volume substantially twice the volume of either cell of said refractive index inter- ferometer.

12. An apparatus as claimed in claim 11, wherein the measuring compartments of both cells of said refractive index interferometer have substantially equal lengths.

13. An apparatus as claimed in claim 10, wherein the measuring compartment of each cell is provided with gas inlet and outlet means in gas flow communication with gas permeable lining means extending longitudinally of the measuring compartment over the whole length thereof, said gas permeable lining means allowing uniform gas distribution or evacuation over substantially the whole compartment length.

14. An apparatus as claimed in claim 13, wherein the measuring compartment of each cell has a cylindrical cross-section which is constant from end to end and wherein said gas permeable lining means comprise a plurality of tubular lining elements of similar wall thickness arranged coaxially in abutting engagement with one another to define an unsealed joint between two adjacent lining elements whereby to permit said uniform gas distribution or evacuation.

15. An apparatus as claimed in claim 10, wherein each interferometer includes a He-Ne laser source means adapted to generate a monochromatic laser beam linearly polarized at 45° and a half-wavelength plate arranged in the optical path of the reference beam issued from said laser team such that said measuring beam and reference beam have respective polarization planes which are perpendicular to one another.

16. An apparatus as claimed in claim 15, wherein each interferometer further includes means for focussing said measuring beam and reference beam after having travelled said predetermined optical path lengths on a grating to produce three beams corresponding to selected superposed diffraction orders including a zero order of diffraction; means for rendering said three beams parallel with one another; a double refracting quartz plate arranged in the optical paths of said three parallel beams with a quarter-wavelength plate being incorporated in the optical path of the beam of the zero order of diffraction to produce three pairs of phase-modulated optical signals, each pair of optical signals being in-phase and anti-phase with one pair being in quadrature with the other two pairs; and means for converting said optical signals into corresponding push-pull modulated electrical signals.

17. An apparatus as claimed in claim 16, wherein the signal converting means of each interferometer has first, second and third outputs associated respectively with said three pairs of push-pull modulated electrical signals, said second output being associated with the pair of signals which is in quadrature with the other two pairs, and wherein said circuitry means comprise first and second differential amplifiers associated with the signal converting means of each interferometer, said first differential amplifier having two inputs and an output and said second differential amplifier having an input and an output, the inputs of said first differential amplifier being connected to the first and third outputs of said signal converting means whereby to produce a d.c. compensated output signal and the input of said second differential amplifier being connected to the second output of said signal converting means; a phase detector having two inputs and an output with the inputs being connected to the outputs of said first and second differential amplifiers whereby to produce a d.c. compensated rotating electrical field at the output of said phase detector; a counter having an input and an output with the input being connected to the output of said phase detector whereby to produce at the output of said counter a fringe count associated with each interferometer; and a micro-processor connected to the counter of each interferometer for processing the fringe count associated therewith together with said predetermined temperature value to obtain the compressibility factor of said gas sample.

18. An optical cell for use in a grating interferometer in which a laser beam is divided into a measuring beam and a reference beam travelling along respective optical paths extending in close parallel relationship over predetermined optical path lengths, said cell comprising a body formed with two elongated bores extending through said body in close parallel relation with one another to define elongated measuring and reference compartments for receiving respectively said measuring beam and reference beam therethrough, each compartment being provided with gas inlet and outlet means in gas flow communication with gas permeable lining means extending longitudinally of the compartment over the whole length thereof, said gas permeable lining means allowing uniform gas distribution or evacuation over substantially the whole compartment length.

19. An optical cell as claimed in claim 18, wherein each compartment has a cylindrical cross-section which is constant from end to end and wherein said gas permeable lining means comprise a plurality of tubular lining elements of similar wall thickness arranged coaxially in abutting engagement with one another to define an unsealed joint between two adjacent lining elements whereby to permit said uniform gas distribution or evacuation.

20. An optical cell as claimed in claim 19, wherein said lining elements are removably inserted inside each compartment and are held in place by window means at the ends of each compartment, said window means sealingly engaging outermost lining elements and being transparent to said measuring beam and reference beam for allowing passage of same therethrough, releasable retaining means being provided for releasably retaining said window means in sealing engagement with said outermost lining elements.

* * * * *

UNITED STATES PATENT AND TRADEMARK OFFICE
CERTIFICATE OF CORRECTION

PATENT NO. : 4,702,604
DATED : October 27, 1987
INVENTOR(S) : Jurgen H. Achtermann et al It is certified that error appears in the above-identified patent and that said Letters Patent is hereby corrected as shown below:

Column 7, line 26, change "walue" to read -- value --;

line 33, equation (10) change "$(L_n n/A_n)$" to read -- $(L_n/A_n)$ --.

Column 8, line 17, after "$B_n$", first occurence, insert a period;

line 29, change "p" to read -- $\rho$ --;

line 36, change "$(n-1)p^{-1}$" to read -- $(n-1)\rho^{-1}$ --.

Column 17, line 19, change "hest" to read -- best --.

Column 20, line 4, change "substan tially" to read -- substantially --;

line 32, change "inter-ferometer" to read -- interferometer --.

Signed and Sealed this

Twenty-seventh Day of September, 1988

Attest:

DONALD J. QUIGG

*Attesting Officer*  *Commissioner of Patents and Trademarks*